United States Patent [19]
Gauri

[11] Patent Number: 4,918,008
[45] Date of Patent: Apr. 17, 1990

[54] PROCESS FOR THE PREPARATION OF PROTEIN HYDROLYSATE AND MEDICAMENTS CONTAINING THESE HYDROLYSATES

[76] Inventor: Kailash K. Gauri, Zur Waldburg 13, D-2359 Lentfohrden, Fed. Rep. of Germany

[21] Appl. No.: 918,253

[22] PCT Filed: Jan. 20, 1986

[86] PCT No.: PCT/EP86/00016
§ 371 Date: Sep. 17, 1986
§ 102(e) Date: Sep. 17, 1986

[87] PCT Pub. No.: WO86/04217
PCT Pub. Date: Jul. 31, 1986

[30] Foreign Application Priority Data
Jan. 18, 1985 [DE] Fed. Rep. of Germany ....... 3501560
May 24, 1985 [DE] Fed. Rep. of Germany ....... 3518828

[51] Int. Cl.⁴ .......................... C12P 21/06; A23J 3/00
[52] U.S. Cl. ...................................... 435/68.1; 514/7; 514/76; 514/773; 514/774; 514/825; 514/913
[58] Field of Search ................ 435/69; 424/95; 514/2, 514/7, 76, 773, 775, 825, 844, 855–865, 885, 913

[56] References Cited
FOREIGN PATENT DOCUMENTS
0106309 4/1984 European Pat. Off. .
04217 7/1986 World Int. Prop. O. .

Primary Examiner—Barry S. Richman
Assistant Examiner—T. J. Wallen
Attorney, Agent, or Firm—Bacon & Thomas

[57] ABSTRACT

Protein hydrolysates are described; they may be obtained by the enzymatic decomposition of whey protein, lactalbumin, α-lactalbumin, β-lactoglobulin, lysozyme, lactoferrin or serum albumin. These products are suitable for pharmaceutical purposes.

26 Claims, No Drawings

PROCESS FOR THE PREPARATION OF PROTEIN HYDROLYSATE AND MEDICAMENTS CONTAINING THESE HYDROLYSATES

The invention concerns a protein hydrolysate obtained from whey protein, lactalbumin, $\alpha$-lactalbumin, lactoferrin, $\beta$-lactoglobulin, lysozyme or serum albumin, a process for the preparation of this hydrolysate and its application for pharmaceutical purposes.

It is known that the proteins of milk consist of caseins and whey proteins. In addition the proteose-peptones with a proportion of the total nitrogen content of cow's milk of approximately 5% may be included in the proteins. The proportion of casein in the total protein content of cow's milk is about 80% and that of the whey proteins about 20%. The caseins represent some of the most intensively researched proteins. In contrast to the original assumptions, they are not uniform bodies. Several fractions have been distinguished to date. However, it is typical of all caseins that they contain phosphorus. They are much more complex and have a much higher molecular weight than the so-called whey proteins. At the present time it is known that they consist of $\beta$-lactoglobulin, $\alpha$-lactalbumin, serum albumin and immunoglobulin.

Investigations by Brantl and Teschemacher (Milchwissenschaft 37, pages 641–644, 1982) showed that opiate-like acting substances may be isolated from the casein fraction of cattle milk. Beginning with commecially available casein-peptone, these authors prepared a 65:35 (v/v) chloroform methanol extract, prepurified it on active carbon and XAD-2-polystyrene resin and further purified it with HPLC. The opiate activity of the material obtained in each case was determined on guinea pig ileum preparations and the enrichment and purification quantatively observed in this manner. The opiate effect was attributed to a heptapeptide and its fragments shortened at the C terminal by one or several amino acid radicals.

It is the object of the invention to prepare further pharmaceutically usable components from certain other proteins.

It was discovered surprisingly that beginning with whey proteins, lactalbumin, $\alpha$-lactalbumin, lactoferrin, $\beta$-lactoglobulin, lysozyme or serum albumin decomposition products may be obtained, which have surprising pharmacological effects.

In particular decomposition products of lactalbumin, $\alpha$-lactalbumin, $\beta$-lactoglobulin, lactoferrin or the mixture of all whey proteins and of denaturated lysozyme, show surprising pharmacological effects. In view of the aforementioned investigations, it has been believed that pharmacologically effective components of milk occur only in the casein fraction. Lysozyme resembles lactalbumin in its structure. In the two proteins, 51 amino acids are arranged identically and 24 in a similar manner. Lysozyme is present in small amounts in cow's milk and in larger proportions in egg protein and in mucous membranes.

The protein hydrolysate according to the invention may be obtained by preparing an approximately 1 to 10 weight % aqueous suspension of whey protein, lactalbumin, lactoferrin, $\alpha$-lactalbumin, $\beta$-lactoglobumin, lysozyme or serum albumin, treating the suspension at 35 to 38° C. under agitation with at least one protease and optionally a lipase, continuing said treatment at approximately 60° C. for several hours, heating the suspension to 80 to 90° C., let it stand at this temperature for a short period of time, allow it to cool, concentrating it under a reduced pressure and isolating the residue as product (A); extracting the residue with a polar solvent or mixture of solvents at room temperature or a slightly elevated temperature, filtering it and obtaining from the filtrate by evaporation to dryness the product (AP).

Advantageously, a 2 to 5% by weight suspension of the initial material in water is used.

The treatment is carried out preferably at 35 to 38° C. over approximately 1 to 4 h, advantageously about 2 h, and the elevated temperature of approximately 60° C. is advantageously maintained for about 2 to 3 h.

As the polar solvent, preferably ethanol, chloroform or isopropanol and as the mixture of polar solvents advantageously a mixture of chloroform/ethanol (1/1 to 3/1 vol/vol) of an ethanol/water mixture with 20 to 80% water, may be used.

As the protease or proteases preferably papain, pancreatin, chymotrypsin and optionally a protease obtained from fungi and/or bacteria are used, with said fungus protease being chosen from among the proteases of the Tritirachium species, in particular *Tritirachium alba*, proteases of the Aspergillus species, in particular *Aspergillus saito, Aspergillus sojae, Aspergillus oryzae* and/or of the Rhizopus species, in particular Newlases, and the bacteria proteases selected from among proteases of Streptomyces species, in particular *Streptomyces caespitosus, Streptomyces griseus (Pronase E), of the Bacillus subtilis* species, in particular Subtilo-peptidase A (Carlsberg Subtilisin), and of *Bacillus polymyxa*.

In the case of an initial material that contains appreciable amounts of starch and starch-like products, it is advantageous to additionally use an $\alpha$-amylase of a Subtilis species. The activity optimum of such an amylase is usually at a pH value of 5.7 to 7.2 and the temperature may be as high as 75° C.

The additional use of a lipase is as a rule necessary only if the initial materials contain appreciable amounts of fats.

Advantageously, the enzymes are used in proportions of approximately 0.01 to 2% by weight with respect to the suspension.

Papain or a mixture of approximately equal parts of pancreatin and papain are used preferably as the protease.

A further advantageous protease mixture consists of a mixture of approximately equal parts of papain, pancreatin and a bacteria or fungus protease, for example the bacteria protease E from *Streptomyces griseus* and as the fungus protease the product "Newlase" from an Aspergillus species.

The more heat resistant enzymes are added preferably in the second heating phase, i.e., after the first heating of 35 to 38° C.

The aforementioned product (AP) may be further purified and separated by suspending it in 10 to 20 times its weight of a 40 to 80% aqueous ethanol, extracting it repeatedly with about the same volume of an aliphatic or cycloaliphatic hydrocarbon with approximately 4 to 8 C atoms, removing the solvent from the individual (aqueous alcohol and hydrocarbon extract) phases, to obtain as the residue of the aqueous alcohol phase the product ($A_2$) and as the residue of the hydrocarbon extract the product (P). The product ($A_2$) is extracted advantageously with about 5 to 20 times its weight of diethylether, the undissolved residue intensively agitated with approximately 20 to 40 times its weight of chloroform, subsequently filtered, the filtrate evaporated to dryness and the product (F) isolated. The portion insoluble in chloroform is the product (N).

To increase the yield, advantageously the ether extract obtained in the treatment of the product ($A_2$) may be concentrated and the residue obtained combined with the aforementioned product (P). The latter may be advantageously dissolved in absolute ethanol for further purification, diluted with $H_2O$ until permanent turbidity and then extracted with an aliphatic or cycloaliphatic hydrocarbon with approximately 4 to 8 C atoms.

Following the removal of the extraction medium a purified product (P) is obtained, which is solid at room temperature but liquid above 30° C.

Advantageously, a further product ($A_2$) may be obtained from aqueous ethanol phase by evaporation, which as described above may be processed further and which in the aforedescribed separation process yields the product (F).

The abovedescribed products (F) and (N) may contain chloroform residues, which may be removed by dissolving the products (F) and (N) in a slight volume of ethanol and drawing off the ethanol in vacuum.

The aforementioned aliphatic and cycloaliphatic hydrocarbons with 4 to 8 C atoms are preferably n-hexane, cyclohexane, heptane, octane or petroleum ether with a boiling range from 40 to 70° C.

The protein hydrolysates that may be obtained by the invention possess valuable pharmacological properties. They have for example, analgetic, antiphlogistic, antimutagen effects and act as an antiglaucoma agent. They may therefore be used to treat painful inflammations of any kind, for example, neurodermatitis, arthritis, rheumatism and also glaucoma. The products (AB) and (A) according to the invention act primarily in an analgetic, antimutagenic and antiphlogistic manner. The product (F) of the invention is characterized particularly by its antiphogistic and antiglaucoma actions.

The product (N) of the invention acts mainly in an analgetic and antimutagenic manner.

The product (P) of the invention is advantageously suitable as an ointment base.

The product (N) of the invention obtained from lactoferrin shows a particularly pronounced antimutagenic action.

The use of the protein hydrolysate according to the invention in prophylactic and therapeutic treatments of the aforementioned diseases is therefore also an object of the present invention.

The invention further relates to pharmaceutical compositions containing at least one of the protein hydrolysates of the invention, optionally together with a pharmaceutically suitable carrier and/or auxiliary substance. These compositions may be used in particular in case of the aforementioned indications; they may be applied for example orally, parenterally or topically. The dosage depends primarily on the specific form of preparation and the purpose of the therapy or prophylaxis.

In the case of oral administration the individual dose is generally between 0.5 and 50 mg (for an adult with a body weight of approximately 70–75 kg) and approximately 3–10 doses are administered per day (24 h). In the treatment of neurodermatitis the doeses may be in the lower range, for example 1.5–3 mg of the active ingredient per single dose. Which such doses, itching disappears rapidly and the skin is subsequently normalized. In the treatment of rheumatism the daily dose by amount to up to 500 mg (for an adult).

In the case of intravenoue administration usually 70–140 mg are given per person (body weight of about 75 kg) per day. As a rule, this dose is given in a single application per day.

In topical applications usually 1 or 2 times the amount of the active ingredient specified for oral administration is given.

A preparation for oral administration may be formulated as a solution, for example in water or alcohol or as a tablet, wherein for the preparation of the tablets the usual, physiologically acceptable filled, binder, disintegrating and lubricating substances may be used. Suitable fillers are for example milk, sugar, cane sugar, starch or cellulose and their derivatives. Usable binders are for example starch, gelatin, sugar, cellulose ether, polymers, for example polyvinylpyrrolidon. Starch and starch ether may be added as disintegrating agents. Suitable lubricating and mold release substances are for example talcum, stearates or silicones and as flow control means highly dispersed silicon oxide or talcum may be applied. The tablets may further be formulated as coated tablets or film tablets. Obviously, the preparation may also be given in conventional soft or hard gelatin capsules.

For injections, conventional sterile, isotonic aqueous solutions may be prepared. The active ingredient may also be stored as a lyophilisate, to be dissolved prior to administration in a suitable aqueous dilutant.

Preparations for topical adninistration may be present in the form of aqueous solutions, lotions, gels, oily solutions, suspensions, fatty or emulsion ointments. A preparation in the form of an aqueous solution may be obtained for example by dissolving the active ingredients according to the invention in an aqueous buffer solution of pH 4 to 7.5 and optionally adding another active ingredient and/or a polymer binder, for example polyvinylpyrrolidone and/or a preservative. The concentration of the active ingredient is about 1 to 10% by weight.

An oily form of application for topical administration is obtained for example by suspending the active ingredients in oil, optionally with the addition of swelling agents, such as aluminum stearate and/or surface active agents (surfactants), the HLB value (hydrophilic-lipophilic balance) is less than 10, such as fatty acid monoesters of multivalent alcohols, for example glycerinstearate, sorbitanmonolaurate, sorbitanmonostearate or sorbitanmonooleate.

A fat-containing ointment may be obtained for example by suspending the active ingredients of the invention in a spreadable fatty base, optionally with the addition of a surface active agent with an HLB value of less than 10.

Product (P) of the invention is an advantageous ointment base.

The antimutangenic effect was determined by means of the sister-chromatide-exchange test on Chinese hamsters; this method is described by H. Marquardt and U. Bayer in Mutation Research 56, 169–176 (1977).

The local analgesia was determined by the so-called Frey hair on the cornea of rabbits, see the paper by M. v. Frey, Contribution to the Physiology of the Sensation of Pain, Bericht uber die Verhandlungen der Koniglich sachsischen Gesellschaft fur Wissenschaften zu Leipzig (Proceedings of the Royal Saxon Society for the Sciences at Leipzig), Mathemt. Physisch. Classe, Leipzig, published by Hirzel (1894), 185-196. Example for the treatment of neurodermatitis:

Twelve patients afflicted by neurodermatitis and therefore experiencing strong itching over their entire body, were given a drop of a 5% solution of product (F) of the invention in 20% aqueous ethanol, three times daily. A second group of 12 patient served as the control group (receiving only aqueous ethanol). In the case of the patients of the group receiving the active ingredient, itching disappeared approximately 30 min after the application. Following a four day treatment, the inflammation of the skin has strongly regressed.

Depending on the protease used, according to the invention primarily antiphlogistically effective peptides are obtained, which generally have only a slight analgesic effect, or a high proportion of analgetically effective peptides. While pancreatin and papain lead mainly to antiphlogistic peptides with protective action against pentoxyphyllin damage, peptides with an additional analgesic action are obtained by the combination of pancreatin and/or papain and proteases from fungi or bacteria. In other words, proteases operating at higher temperatures, for example those from fungi and bacteria, lead to a high proportion of analgetically effective peptides.

The following examples are intended to explain the preparation of the substances according to the invention further.

EXAMPLE 1

5 g of a denaturated milk protein fraction of whey (commercially available as lactalbumin, for example as lactalbumin-sigma) are suspended in 95 ml water, 0.4 g of a mixture of approximately equal proportions of pancreatin, papain and a bacteria or fungus protease is added under agitation, and the mixture heated to 35 to 37° C. At this temperature the mixture is stirred for several hours, until is is clear. The reaction mixture is then heated to 60° C., the temperature slowly raised to 80° C. after about 1 h, maintained at this temperature for a short period of time, cooled and evaporated in vacuum. The residue is taken up in 100 ml ethanol/water 70:30 (v/v), mixed with slight amounts of active carbon and celite, filtered and the filtrate evaporated to dryness. A colorless product with an approximate yield of 70-80% isobtained.

EXAMPLE 2

5 g lactalbumin are suspended in 130 ml water, 50 mg papain and 50 mg pancreatin and 50 mg of a lipase are added, the mixture heated to 35 to 37° C., agitated at this temperature for about 2 h, whereupon 50 mg of a commercial fungus protease, for example Newlase, are added and the temperature raised slowly (over about 2-3 h) to 60° C. The temperature is then briefly raised to 80° C., the mixture allowed to cool, the turbid solution evaporated in vacuum, the residue taken up in ethanol, filtered and evaporated in vacuum. Approximately 0.2 g of product (AP) is obtained.

EXAMPLE 3

In a manner similar to Example 1, 5 g lactalbumin are suspended in 130 ml water. 50 mg each of two proteolytic enzymes, for example papain and pancreatin, are added, the suspension heated to 38° C. and agitated for about 2 h at this temperature. The temperature is then raised to 80° C. and processed as in Example 1. 1.8 g of the product is obtained.

EXAMPLE 4

In a manner similar to Example 1, 5 g lactalbumin are suspended in 130 ml water. 50 mg papain are added, the suspension heated to 35°-37° C., agitated for 1 h at this temperature, another 50 mg papain added, the suspension further agitated at this temperature for about 2 h, briefly heated to 80° C. and the mixture evaporated after cooling in a vacuum to dryness. If the residue is then treated with ethanol/water as in Example 1, 1.7 g of a product is obtained.

EXAMPLE 5

5 g lactalbumin are suspended and treated as in Example 4, but in place of the papain, in this case pancreatin is used. After the alcohol/water treatment about 2.1 of a product are obtained.

EXAMPLE 6

5 g lactoblobulin or 5 g lactoferrin are hydrolyzed after the addition of 200 ml water with a mixture of 50 mg each of pancreatin, papain and a fungus protease, as described in Example 1 and processed. After precipitation with 70:30 ethanol:water, 5.6 g of a peptide mixture are obtained.

Different products are used as fungus proteases. In one initial preparation as the enzyme mixture a lyophilized powder from a Tritirachium species, in particular Tritirachium alba with a protein content of approximately 90% and an activity of about 10 to 20 E/mg protein, is used. In another initial preparation proteases from an Aspergillus species, in particular *Aspergillus saito* with an activity of approximately 0.3 E/mg of the dry mass or *Aspergillus sojae* with the same activity or *Aspergillus oryzae*, are used. In a further initial mixture proteases from Rhizopus species, with an activity of about 0.5 E/mg of the mass are used. The enzyme is also known as "Newlase".

In each case a protective effect with respect to 300 mg/kg i.p. pentoxyphyllin is obtained with the lactoglobulin-peptide-hydrolysate in a dose of 250 mg/kg.

EXAMPLE 7

As described in Example 6, 1 g α-lactoglobulin is hydrolyzed with pancreatin, papain and a bacteria protease (from yeast) in quantities of 10 mg each and processed as described above.

The enzyme mixture is prepared by decapsulation with 50% ethoxylated fatty alcohol. It is an endopeptidase with an activity of approximately 440 Delft units /mg of the dry mass. The density of the protein amounts to 750 to 900 g/l. Optimum activity is at pH 7 to 11 and a temperature of approximately 60° C.

Further initial mixtures are prepared by the use of *Streptomyces species*, in particular *Streptomyces caespitosus* with an activity of 0.7 to 1 E/mg of the dry mass, with *Subtilis species* with an activity of 7-15 E/mg protein, in particular the Subtilopeptidase A enzyme (Carlsberg Subilisin), with *Streptomyces griseus* (pronase E) with an activity of 4 E/mg of the dry mass, purified, or Streptomyces griseus with an activity of 15 to 20 E/mg of the dry mass, or with *Bacillus polymyxa* with an activity of about 0.4 E/mg of the dry mass.

EXAMPLE 8

5 g β-lactalbumin are hydrolyzed and processed as in Example 6. The yield is 5.5 g.

EXAMPLE 9

100 g α-lactalbumin are hydrolyzed as in Example 6. In the processing, in place of the ethanol/water mixture, absolute ethanol is used. The yield is approx. 2.5 g. The peptide mixture exhibits a local analgesic effect with concentrations of 0.3 to 3%.

EXAMPLE 10

5 g lysozyme from egg protein are denatured in 200 ml $H_2O$ at 80° C., cooled to 38° C., hydrolyzed with an enzyme mixture as in Example and processed as described in Example. 3.4 g of a colorless product with antimutagenic, antiphlogistic and local analgesic actions are obtained. The product according to the invention was tested pharmacologically in experiments with mice, in the following manner. A pentoxyphyllin dose of approx. 300 mg/kg, i.p. is normally lethal for a mouse. If, however, approximately 30 min earlier the product of the invention is administered in a dose of approx. 300 to 600 mg/kg intraperitoneally or intravenously, a 60 to 100% protective effect is obtained against the pentoxyphyllin-induced mortality.

The local analgesic action was also tested on human eyes. The antimutagenic effect was determined by the Hamster-Sister Chromatide Exchange Test.

EXAMPLE 11

5 g of the raw product of Example 1 are extracted with 100 ml absolute ethanol at a temperature between 22° and 50° C. The clear solution obtained is filtered or centrifuged and evaporated to dryness, whereby about 0.2 g of product (AP) is obtained as the residue.

The analgetic effect of this product is so pronounced that only ⅛ of the amount of the product of Example 1 is required to achieve the same pharmacological effect.

EXAMPLE 12

100 g of the product (AP) obtained according to Example 11 are suspended in 500 ml 80% ethanol and extracted twice with 500 ml heptane each. The heptane phase is washed with 200 ml 80% ethanol (the wash solution is combined with the ethanol phase). Subsequently, the heptane is drawn off. The residue is the product (P). Yield: 43 g. By evaporating the aqueous-alcohol phase, the product ($A_2$) is obtained. Yield: 54 g. The latter is vigorously agitated with 1.5 l diethylether for one-half hour, the ether phase decanted, the residue isolated and vigorously stirred with one liter chloroform. The chloroform phase is later filtered off, evaporated in vacuum and the product (F) obtained as the evaporation residue. Yield: 20 g.

The chloroform soluble filter residue is taken up in 250 ml ethanol and evaporated in vacuum. The product (N) is obtained; yield: 13 g. By dissolution in 200 ml chloroform and evaporation of the chloroform phase an additional 4 g of product F are obtained. The yield in product (N) is then 8.5 g.

Product (F) may again be taken up in ethanol for the complete removal of the chloroform residues and freed in vacuum of all volatile components.

From the product (P) obtained above, by dissolution in absolute ethanol, the addition of water to permanent turbidity and subsequent extraction with heptane, a further product ($A_2$) may be obtained from the ethanol phase (approx. 10% of the product P used).

I claim:

1. Protein hydrolysate prepared by a process comprising:
    heating an approximately 1% to 10% by weight suspension of a member selected from the group consisting of whey protein, lactalbumin, α-lactalbumin, lactoferrin, β-lactoglobulin, lysozyme or serum albumin in water at 35° C. for about 1 to 4 hours under agitation with at least one protease,
    continuing said heating at about 60° C. for about 2 to 3 hours,
    heating the suspension to 80° C. to 90° C. and maintaining it at this temperature for a brief time period,
    cooling the suspension and evaporating it under reduced pressure to produce a residue,
    isolating the residue as product (A) and extracting it with a member selected from the group consisting of a polar solvent or a mixture selected from the group consisting of a polar solvent or a mixture of polar solvents at room temperature or at an elevated temperature up to 50° C. to produce an extract, and
    filtering the extract to obtain a filtrate and obtaining from the filtrate product (AP) by evaporating the filtrate to dryness.

2. Protein hydrolysate according to claim 1, wherein said suspension is heated with a lipase in addition to said at least one protease.

3. Protein hydrolysate prepared by a process comprising:
    heating an approximately 1% to 10% by weight suspension of a member selecteds from the group consisting of whey protein, lactalbumin, α-lactalbumin, lactoferrin, β-lactoglobulin, lysozyme or serum albumin in water at 35° C. to 38° C. for about 1 to 4 hours under agitation with at least one protease,
    continuing said heating at about 60° C. for about 2 to 3 hours,
    heating the suspension to 80° C. to 90° C. and maintaining it at this temperature for a brief time period,
    cooling the suspension and evaporating it under reduced pressure to produce a residue,
    isolating the residue as product (A) and extracting it with a member selected from the group consisting of a polar solvent or a mixture of polar solvents at room temperature or at an elevated temperature up to 50° C. to produce an extract, p1 filtering the extract to obtain a filtrate and obtaining from the filtrate product (AP) by evaporating the filtrate to dryness,
    suspending product (AP) in approximately 10 to 20 times its weight of 40% to 80% aqueous ethanol to produce a suspension,
    extracting the suspension with about the same volume of a member selected from the group consisting of an aliphatic or cycloaliphatic hydrocarbon with 4 to 8 C atoms to produce an aqueous alcohol and a hydrocarbon extract,
    removing solvent from individual phases of the aqueous alcohol and the hydrocarbon extract to obtain a residue of the aqueous alcohol phase, product ($A_2$) and a residue of the hydrocarbon extract, product (P),
    extracting the product ($A_2$) with about 5 to 20 times its weight of chloroform to produce an undissolved portion of product ($A_2$), agitating the undissolved portion of the product ($A_2$) with about 20 to 40 times its weight of chloroform to produce an extract, filtering the extract and evaporating the filtrate to dryness, thereby isolating a product (F), and isolating the portion of product ($A_2$) which is insoluble in chloroform as product (N).

4. Pharmaceutical preparations containing at least one protein hydrolysate claimed in claims 1, 2, or 3 and a pharmaceutically acceptable carrier.

5. Process for preparation of protein hydrolysates comprising:

heating an approximately 1% to 10% by weight suspension of a member selected from the group consisting of whey protein, lactalbumin, α-lactalbumin, lactoferrin, β-lactoglobulin, lysozyme or serum albumin in water at 35° C. to 38° C. under agitation with at least one protease, heating the suspension to about 60° C. under agitation, heating the suspension to 80° C. to 90° C., cooling the suspension and evaporating it under reduced pressure and isolating the residue as product (A), extracting the residue with a member selected from the group consisting of a polar solvent and a mixture of polar solvents at room temperature or an elevated temperature to obtain an extract, and filtering the extract and evaporating the filtrate to dryness to obtain the product (AP).

6. Process according to claim 5, wherein said suspension is heated with a lipase in addition to said at least one protease.

7. Process according to claim 6, wherein said at least one protease and said lipase are used in a proportion of about 0.01% to 2% by weight with respect to the suspension.

8. Process according to claim 6, wherein said lipase is used in a proportion of about 0.01% to 2% by weight with respect to the suspension.

9. Process according to claim 5, wherein a 2% to 5% by weight suspension in water is used.

10. Process according to claim 5, wherein the treatment at 35° C. to 38° C. extends over 1 to 4 hours and that the treatment at about 60° C. is maintained for about 1 to 4 hours.

11. Process according to claim 10, wherein the treatment at 35° C. to 38° C. extends for about 2 hours and that the treatment at about 60° C. is maintained for about 2 to 3 hours.

12. Process according to claim 5, wherein the residue is extracted with a polar solvent which is a member selected from the group consisting of absolute ethanol, chloroform, and isopropanol.

13. Process according to claim 5, wherein said protease is a member selected from the group consisting of papain, pancreatin, chymotrypsin, and trypsin.

14. Process according to claim 5, wherein said at least one protease is used in a proportion of about 0.01% to 2% by weight with respect to the suspension.

15. Process according to claim 5, wherein papain is used as the protease.

16. Process according to claim 5, wherein a mixture of approximately equal weights of pancreatin and papain is used.

17. Process according to claim 5, wherein a mixture of approximately equal parts by weight of papain, pancreatin, and a member selected from the group consisting of bacterial or fungus protease is used.

18. Process according to claim 5, wherein heat resistant enzymes are added to the suspension after the first heat treatment to 35° C. to 38° C.

19. Process according to claim 5, further comprising:

suspending product (AP) in approximately 10 to 20 times its weight of 40% to 80% aqueous ethanol, extracting the suspension with about the same volume of a member selected from the group consisting of an aliphatic or cycloaliphatic hydrocarbon with 4 to 8 C atoms to produce an aqueous alcohol extract and a hydrocarbon extract, removing the solvent from the aqueous alcohol and the hydrocarbon extract to obtain a residue of the aqueous alcohol phase, product ($A_2$) and a residue of the hydrocarbon extract, product (P), extracting product ($A_2$) with about 5 to 20 times its weight of chloroform to obtain an undissolved portion of the product ($A_2$), agitating the undissolved portion of the product ($A_2$) with about 20 to 40 times its weight of chloroform to obtain an extract, filtering the extract to obtain a filtrate and evaporating the filtrate to dryness, thereby isolating product (F), and isolating the chloroform insoluble portion of the product ($A_2$) as the product (N).

20. Process according to claim 5, wherein said protease is obtained from fungi.

21. Process according to claim 20, wherein said fungus proteases are members selected from the group consisting of proteases from the Tritirachium species, proteases from the Aspergillus species, and proteases form the Rhizopus species.

22. Process according to claim 21, wherein said fungus proteases are members selected from the group consisting of proteases from *Tritirachium alba*, proteases from *Aspergillus asito, Aspergillus sojae* and *Aspergillus oryzae* and Newlase.

23. Process according to claim 5, wherein said protease is obtained from bacteria.

24. Process according to claim 23, wherein said bacteria proteases are members selected from the group consisting of proteases of the Streptomyces caespitosus species, proteases of the *Bacillus subtillis* species, and proteases of the *Bacillus polymixa* species.

25. Process according to claim 24, wherein said bacteria proteases are members selected from the group consisting of *Streptomyces caespitosus, Streptomyces griseus* (Pronase E) and Subtilopeptidase A (Carlsberg Subtilisin).

26. Process according to claim 5, wherein the residue is extracted with a mixture of polar solvents which is a member selected from the group consisting of 1/1 to 3/1 vol/vol chloroform/methanol mixture and an ethanol/water mixture with 20% to 80% vol. water.

* * * * *